United States Patent
Huddle et al.

(10) Patent No.: US 9,439,785 B2
(45) Date of Patent: Sep. 13, 2016

(54) DISCRETELY ADJUSTABLE HIP-REPLACEMENT TRIAL

(71) Applicant: Zimmer, Inc., Warsaw, IN (US)

(72) Inventors: Adam Christopher Huddle, Golden, CO (US); Robert D. Krebs, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 110 days.

(21) Appl. No.: 14/296,677

(22) Filed: Jun. 5, 2014

(65) Prior Publication Data

US 2015/0018961 A1 Jan. 15, 2015

Related U.S. Application Data

(60) Provisional application No. 61/846,273, filed on Jul. 15, 2013.

(51) Int. Cl.
- *A61F 2/46* (2006.01)
- *A61F 2/36* (2006.01)
- *A61F 2/30* (2006.01)

(52) U.S. Cl.
CPC ............ *A61F 2/4684* (2013.01); *A61F 2/3607* (2013.01); *A61F 2/3609* (2013.01); *A61F 2002/30505* (2013.01); *A61F 2002/30551* (2013.01); *A61F 2002/3652* (2013.01)

(58) Field of Classification Search
CPC .............. A61F 2/3607; A61F 2/4607; A61F 2002/30551; A61F 2002/3652; A61F 2/4684
See application file for complete search history.

(56) References Cited

U.S. PATENT DOCUMENTS

| | | | |
|---|---|---|---|
| 4,601,289 A | 7/1986 | Chiarizzio et al. | |
| 5,074,879 A * | 12/1991 | Pappas | A61F 2/30724 623/23.46 |
| 5,201,882 A | 4/1993 | Paxson | |
| 5,800,557 A * | 9/1998 | Elhami | A61B 17/1753 623/23.12 |
| 5,888,208 A | 3/1999 | Ro | |
| 6,193,759 B1 * | 2/2001 | Ro | A61F 2/4607 623/23.18 |
| 7,425,214 B1 | 9/2008 | McCarthy et al. | |
| 7,854,737 B2 | 12/2010 | Daniels et al. | |
| 7,951,205 B2 | 5/2011 | McCleary et al. | |
| 8,333,807 B2 | 12/2012 | Smith et al. | |
| 2004/0054419 A1 | 3/2004 | Serra et al. | |
| 2004/0122437 A1 * | 6/2004 | Dwyer | A61F 2/4657 606/87 |
| 2011/0224798 A1 * | 9/2011 | Caillouette | A61F 2/36 623/22.11 |
| 2012/0259424 A1 | 10/2012 | Hood et al. | |

FOREIGN PATENT DOCUMENTS

WO WO-9600539 A1 1/1996

* cited by examiner

*Primary Examiner* — Thomas J Sweet
*Assistant Examiner* — Megan Wolf
(74) *Attorney, Agent, or Firm* — Schwegman Lundberg & Woessner, P.A.

(57) ABSTRACT

Hip replacement surgery (hip arthroplasty) includes implantation of a distal stem into a femur of a patient, and implantation of a proximal body to connect to the distal stem. A practitioner uses a "trial" or "provisional" to determine a suitable size and configuration for the implantable proximal body, then selects a suitable proximal body from a set of differently sized and shaped proximal bodies. The trial adjusts discretely, as opposed to continuously, and has discrete settings that correspond to the sizes and configurations available in the set of implantable proximal bodies. In some examples, the trials are provided as a kit of parts, where each part in the kit is adjustable for height (i.e., the length of the femur). The parts in the kit can have different, fixed, values for offset (i.e., the lateral distance of the femur to the center of the femoral head in the acetabulum).

18 Claims, 6 Drawing Sheets

DISCRETELY ADJUSTABLE HIP-REPLACEMENT TRIAL

CLAIM OF PRIORITY

This application claims the benefit of U.S. Provisional Patent Application Ser. No. 61/846,273, filed on Jul. 15, 2013, the benefit of priority of which is claimed hereby, and which is incorporated by reference herein in its entirety.

BACKGROUND

A human hip joint connects a femur (sometimes referred to as a thigh bone) to an acetabulum (sometimes referred to as a hip socket) of the pelvis. Hip joints support the weight of a human body, and are important for retaining balance.

Some types of injury, disease, or degeneration can produce pain and/or restricted motion in a hip joint. One treatment for certain types of damage to a hip joint is surgery. For severe damage, the hip can be surgically replaced.

OVERVIEW

Hip replacement surgery (hip arthroplasty) can include implantation of a distal stem into a femur of a patient, and implantation of a proximal body to connect to the distal stem. Implantable proximal bodies can be presented to a practitioner in the form of a set. The implantable proximal bodies in the set can include discrete combinations of the parameters of height (i.e., the length of the femur) and offset (i.e., the lateral distance from the central axis of the femur to the center of the femoral head in the acetabulum). Height and offset are established quantities in the field of hip replacement surgery.

FIG. 1 shows an exemplary set 1 of implantable proximal bodies. The set 1 includes twelve parts, each part being a different combination of height and offset.

In general, the values of height and offset in the set 1 are selected to accommodate the anatomy of most patients, so that at least one of the twelve permutations ensures a suitable fit for the implantable proximal body. In the example of FIG. 1, there are four values of height, including 60 mm, 70 mm, 80 mm, and 90 mm. In the example of FIG. 1, there are three values of offset, including 35 mm, 40 mm, and 45 mm. The values of height and offset in FIG. 1 are but one example, and that other suitable values may also be used.

In order to determine the most appropriate height and offset for a particular patient, a practitioner uses a "trial" or "provisional", which is shaped and sized similar to the implantable parts, but is removable and can be reused or disposed of. In conventional practice, a practitioner tries on various sizes by temporarily attaching the trial to a stem, and noting the fit of the trial with the anatomy of the patient. Once a best fit is found, the practitioner notes the values of height and offset of the trial that provides the best fit. The practitioner removes the trial, selects an implantable proximal body from the set 1, the selected body having height and offset values that are closest to the noted values, and implants the selected implantable proximal body.

FIG. 2 is a schematic drawing of an exemplary kit 10 of adjustable trials. A practitioner can use the trial kit 10 for determining a suitable height and offset of an implantable proximal body for hip replacement surgery. The trial kit 10 includes a fixed portion 20, and several adjustable portions 30 that can releasably lock to the fixed portion 20 at discrete locations. A practitioner selects one of the adjustable portions 30, which has a particular, fixed, value of offset associated with it, and slides it from discrete location to discrete location along the fixed portion 20 to determine a fit of the trial at various heights.

The fixed portion 20 can removably attach to an upper end of a stem 40. The stem 40 can be implanted at an upper end of a femur of a patient, or can be a trial part that is removably disposed at the upper end of the femur. The stem 40 is not part of the trial kit 10. The fixed portion 20 has a longitudinal axis (A) extending in a vertical direction.

The fixed portion 20 has a plurality of indentations 25A, 25B, 25C, 25D on its exterior surface at specified locations along the longitudinal axis. In the example of FIG. 1, there are four indentations, corresponding to the height values of implants in the set 1; in other examples, there may be two, three, five, six, or more than six indentations.

The trial kit 10 includes a plurality of adjustable portions 30A, 30B, 30C, each with a different value of offset. In the example of FIG. 1, there are three adjustable portions, corresponding to the offset values of implants in the set 1; in other examples, there may be two, four, five, six, or more than six adjustable portions. The adjustable portions 30A, 30B, 30C are intended to be used one at a time, in combination with the fixed portion 20. Each adjustable portion 30A, 30B, 30C slides vertically along the fixed portion 20.

Each adjustable portion 30A, 30B, 30C includes a movable element 35A, 35B, 35C that is biased to contact the exterior surface of the fixed portion 20, such as by spring loading. As the adjustable portion 30A, 30B, 30C slides along the fixed portion 20, the movable element 35A, 35B, 35C snaps into one of the indentations 25A, 25B, 25C, 25D. The snapping releasably locks the adjustable portion 30A, 30B, 30C to the fixed portion 20.

Each adjustable portion 30A, 30B, 30C can have a hand-deployed release mechanism, which can retract the movable element 35A, 35B, 35C from one of the indentations 25A, 25B, 25C, 25D and unlock the adjustable portion 30A, 30B, 30C from the fixed portion 20.

FIG. 3 is a schematic drawing of an adjustable trial 50, as used during a surgical procedure. The adjustable trial 50 can be part of the trial kit 10 of FIG. 1. Prior to surgery, a practitioner can examine one or more X-rays or other images of the anatomy of the patient. The anatomy images can provide the practitioner with a good estimate of the offset value, and, optionally, a rough estimate of the height value. During surgery, the practitioner selects an adjustable portion 30 that has an offset value that best corresponds to the estimate. The practitioner slides the selected adjustable portion 30 vertically along the fixed portion 20 from indentation to indentation, checking a fit of the trial at each height value, in order to determine a best height value. The adjustable portion 30 locks at each indentation, so that the practitioner can determine how well the particular offset and height values fit the patient while the adjustable trial 50 is in the locked position.

In some examples, if the practitioner wishes to determine a fit with more than one offset value, the practitioner can remove one adjustable portion from the fixed portion 20 and use another adjustable portion from the trial kit 10. Once the practitioner has determined the offset and height values that provide the best fit for the patient, the practitioner notes the best fit offset and height values, removes the adjustable portion 30 from the fixed portion 20, removes the fixed portion 20 from the stem 40, selects an implantable proximal body having the noted best fit offset and height values, and surgically implants the selected implantable proximal body onto the stem 40. Following the surgery, the adjustable trial 50, as well as other adjustable trials in the trial 10, can be cleaned, sterilized, and reused for subsequent surgical procedures. Alternatively, the adjustable trial 50 can be designed for a single use, and can be disposed of following a procedure.

There are several advantages to using the trials discussed herein. For instance, a kit of the adjustable trials can include fewer parts than a comparable kit of non-adjustable trials. For example, in the trial kit 10 in FIG. 2, the kit includes three parts, plus a fixed portion, compared with the twelve parts that would be required from the comparable kit of non-adjustable trials. In addition, adjusting the trial during surgery can be significantly quicker than removing one non-adjustable trial from the distal stem and attaching another non-adjustable trial to the distal stem. This can save time and effort for a practitioner.

It will be understood that the adjustable portions and fixed portions shown in FIGS. 2 and 3 are but high-level schematic representations of these parts. In practice, the actual parts can include multiple elements and features that are not shown in FIGS. 2 and 3. FIGS. 4-7 show an exemplary full mechanical configuration for an adjustable trial 100.

This Overview is intended to provide examples of the present patent document. It is not intended to provide an exclusive or exhaustive explanation of the invention. The Detailed Description below is included to provide further information about the present adjustable trial, kit of adjustable trials, and the corresponding methods.

BRIEF DESCRIPTION OF THE DRAWINGS

In the drawings, which are not necessarily drawn to scale, like numerals describe similar components in different views. The drawings illustrate generally, by way of example, but not by way of limitation, various embodiments discussed in the present patent document.

DETAILED DESCRIPTION

Figure 4:
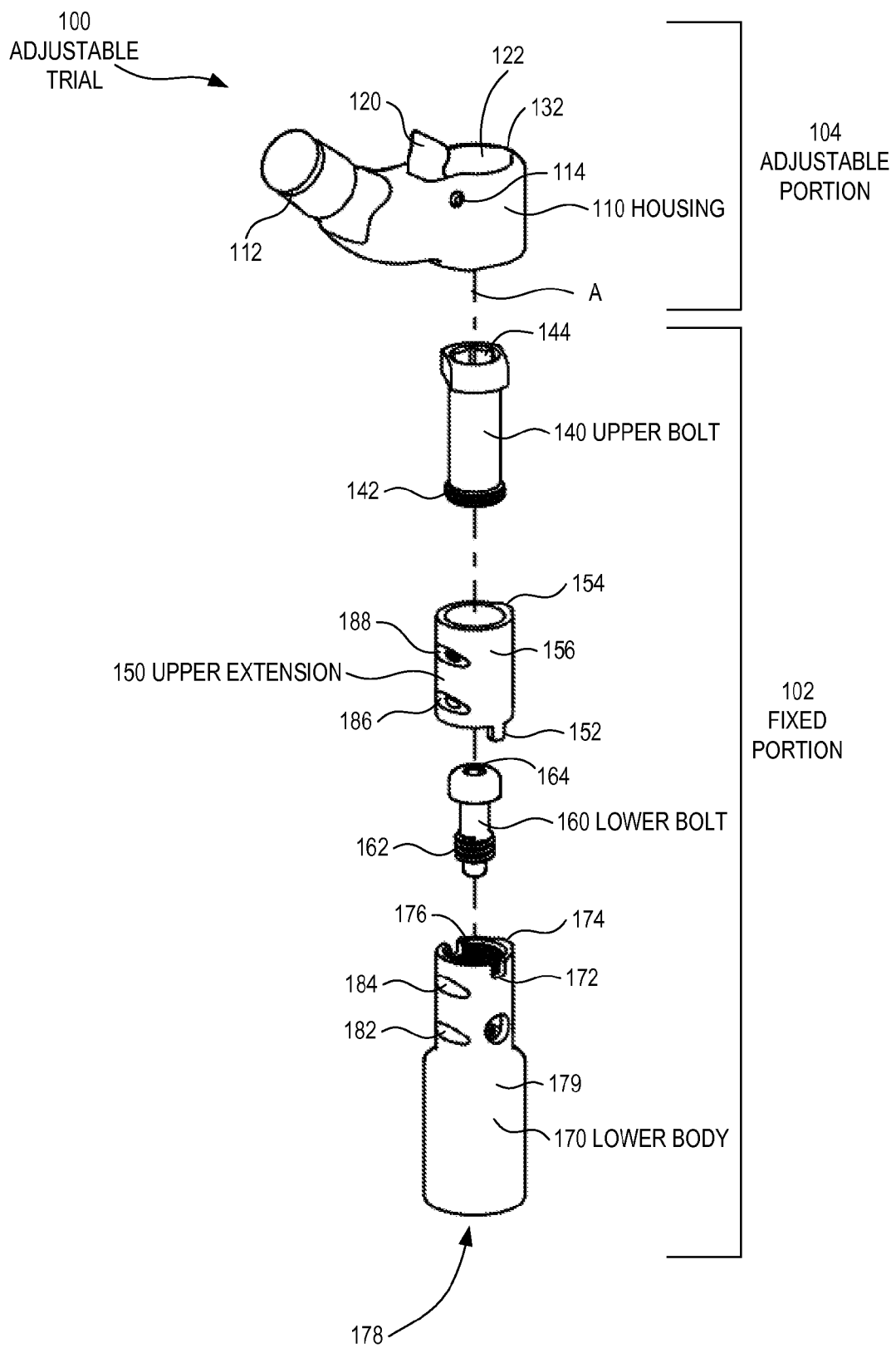
FIG. 4 is an exploded view of an exemplary adjustable proximal trial.

FIG. 4 is an exploded view of the elements in an exemplary adjustable trial. The example adjustable proximal trial 100 includes a fixed portion 102, which removably attaches to a stem, and an adjustable portion 104, which releasably attaches at discrete locations to the fixed portion 102.

Figure 1:
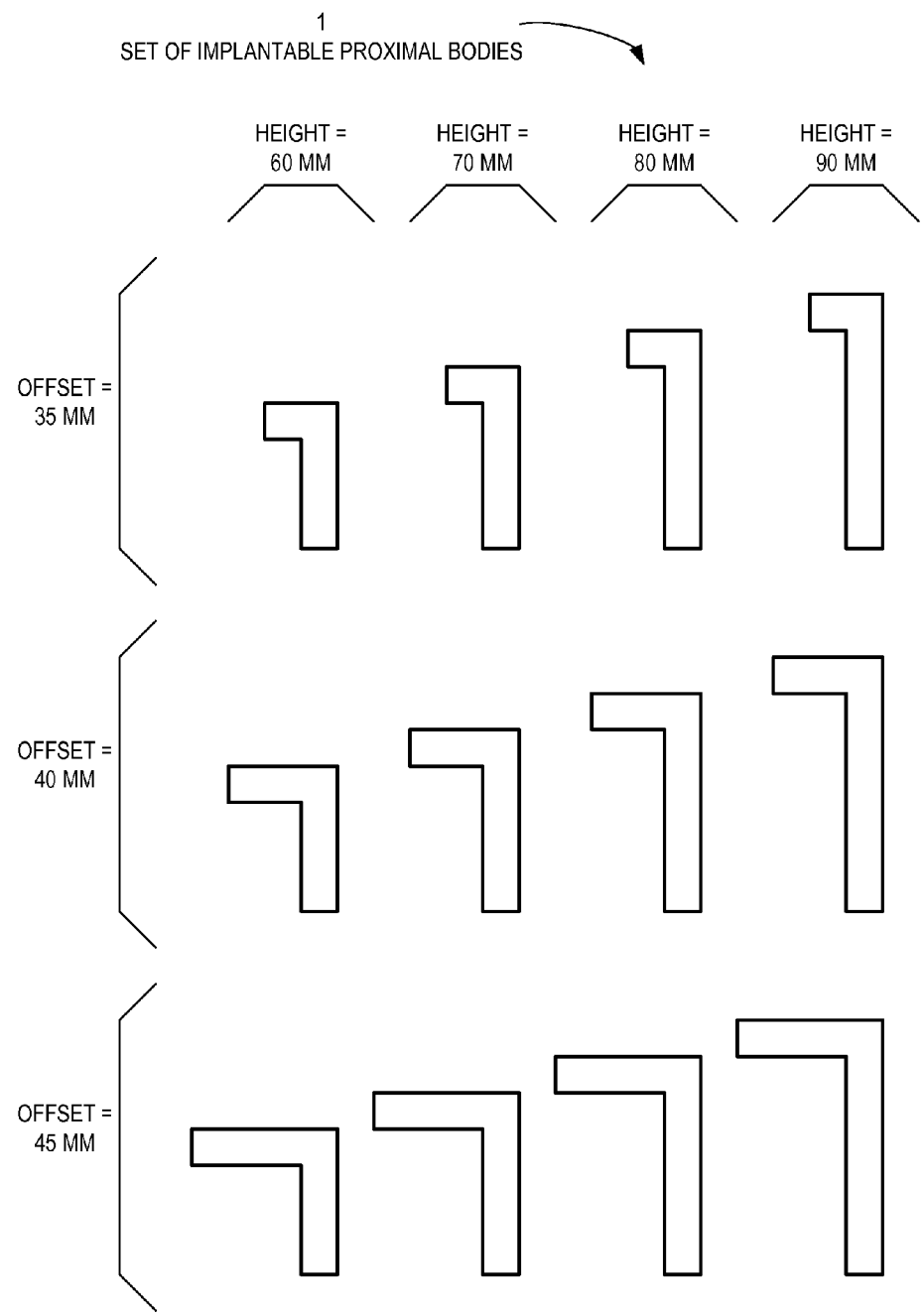
FIG. 1 is a schematic drawing of an exemplary set of implantable proximal bodies.

The fixed portion 102 includes four elements 170, 160, 150, 140, all of which are coaxial with a longitudinal axis (A) of the fixed portion 102. A lower body 170 attaches to an upper end of the distal stem, a lower bolt 160 attaches the lower body 170 to the distal stem 40 (FIG. 1), an optional upper extension 150 upwardly extends the length of the lower body 170, and an optional upper bolt 140 attaches upper extension 150 to the lower body 170. Breaking the longitudinal length of the fixed portion 102 into two portions, namely the lower body 170 and the upper extension 150, allows the lower bolt 160 to be tightened and loosened using a common tool, such as a standard hex key, rather than an elongated, customized tool.

Figure 2:
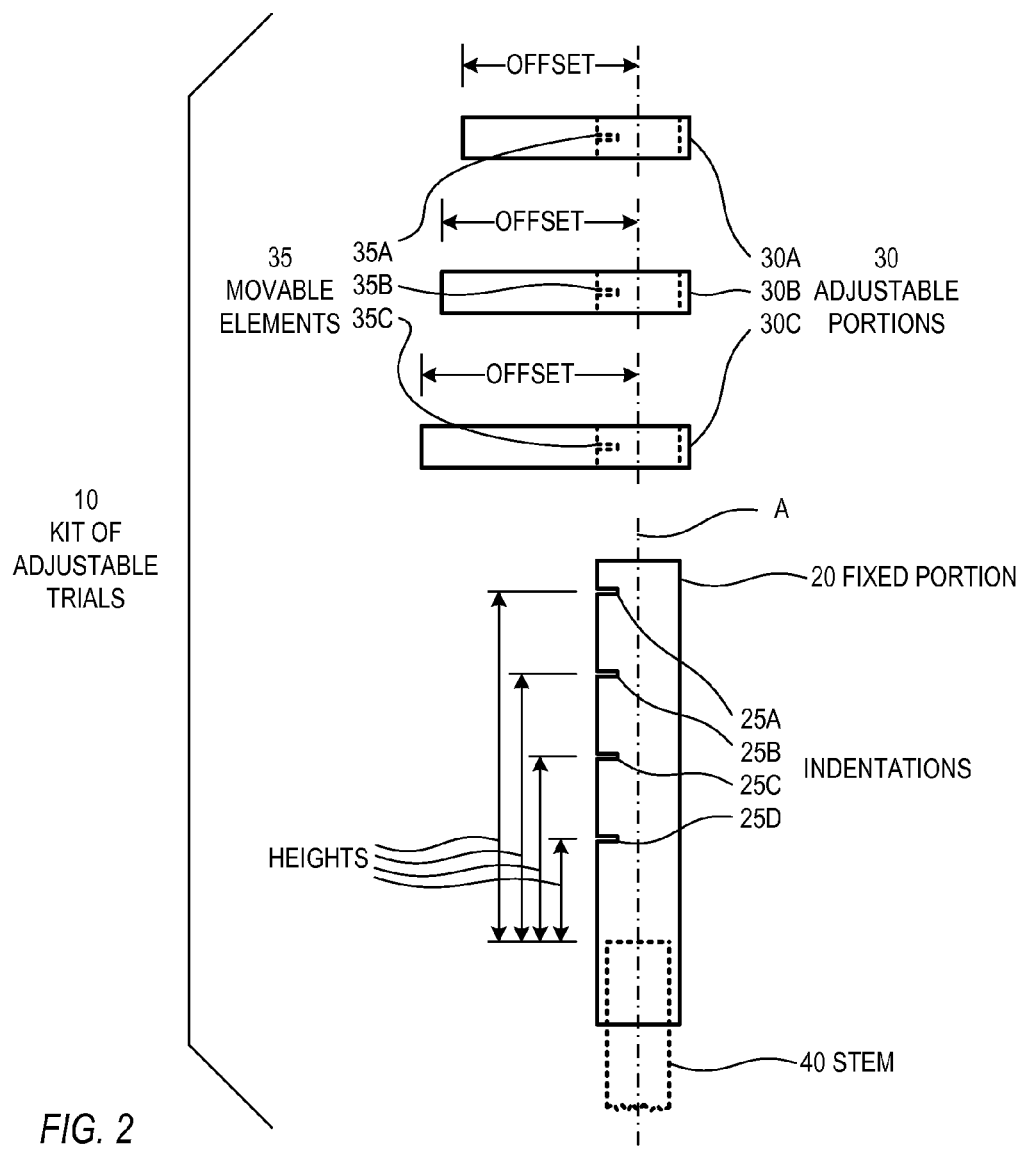
FIG. 2 is a schematic drawing of an exemplary system of adjustable trials.
Figure 3:
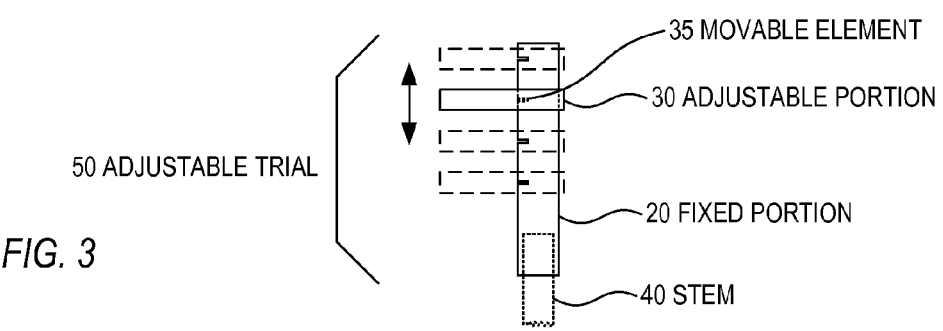
FIG. 3 is a schematic drawing of an adjustable trial, as used during a surgical procedure.

FIG. 4 shows the lower body 170 being generally cylindrical in shape, with the longitudinal axis (A) extending vertically from the proximal (upper) direction to the distal (lower) direction. The lower body 170 has a cylindrical volume 178 in its interior. The cylindrical volume 178 can be accessed from a lower end of the lower body 170. During operation, the upper end of the distal stem extends into the cylindrical volume 178 of the lower body 170, as shown in FIGS. 2 and 3. The wall of the cylindrical volume 178 is sized and shaped to match an exterior surface of the distal stem, so that the lower body 170 can fit snugly, but removably, over the upper end of the distal stem.

An upper end of the lower body 170 can include one or more notches 172 around its circumference. The notches 172 can seat the upper extension 150 thereon during assembly of the device. In some examples, the upper end of the lower body 170 can be crenellated instead. The purpose is to prevent rotational misalignment between the upper and lower bodies. The lower body 170 includes female threads 176 at its upper end, which can couple with corresponding male threads 142 on the upper bolt 140.

The lower body 170 can include an optional keying feature, which can prevent or reduce angular misalignment about the longitudinal axis (A) between the adjustable portion 104 and the fixed portion 102 while still allowing these two pieces to slide vertically along axis A. Such a keying feature can be an elongation or irregularity on an outer profile of the fixed portion 102, which mates with a complementary elongation or irregularity on an inner bore 122 within the adjustable portion 104. For instance, the fixed portion 102 of FIG. 4 includes a spine 174, which extends longitudinally along an outer edge of the lower body 170. The spine 174 can extend into a corresponding groove 132 in the adjustable portion 104. Other suitable keying features may also be used.

An exterior surface 179 of the lower body 170 includes one or more indentations 182, 184. In some examples, the indentations 182, 184 are disposed along a line parallel to the longitudinal axis (A). In some examples, one or more of the indentations 182, 184 extend partially or fully through a wall of the lower body 170. In some examples, the indentations 182, 184 and the spine 174 are on opposite sides of the lower body 170. In the example of FIG. 4, there are two indentations 182, 184 on the lower body 170; in other examples there can be zero, one, three, four, or more than four indentations on the lower body 170.

The lower bolt 160 attaches the lower body 170 to the distal stem. When a practitioner installs an adjustable trial, the practitioner places the lower body 170 over the upper end of the distal stem, then installs the lower bolt 160 to secure the lower body 170 to the distal stem. The lower bolt 160 includes male threads 162 at or near its lower end. When installed, the male threads 162 engage corresponding female threads on the upper end of the distal stem. The lower bolt 160 can be tightened and loosened by inserting a suitable key into one or more sockets 164 at its upper end. In the specific example of FIG. 4, the socket 164 is sized and shaped to accommodate a 3.5 mm hex key; other suitable socket sizes and shapes can also be used.

The upper extension 150 upwardly lengthens the lower body 170. The upper extension 150 is cylindrical in shape, with an open upper end and an open lower end. The upper extension 150 is sized to match the size and shape of the upper end of the lower body 170. The upper extension 150 can include one or more teeth 152 at its lower end, to couple with corresponding notches 172 at the upper end of the lower body 170. In some examples, the lower end of the upper extension 150 is crenellated, with a complementary crenellation to that of the upper end of the lower body 170. In other examples, one or more teeth can be disposed on the upper end of the lower body 170, and one or more notches can be disposed on the lower end of the upper extension 150. The upper extension 150 can include a spine 154 that aligns with the spine 174 on the lower body 170. The spines 154, 174 can extend into a corresponding groove 132 in the adjustable portion, and can be a keying feature of the fixed portion 102. An exterior surface 156 of the upper extension 150 includes one or more indentations 186, 188. In some examples, the indentations 186, 188 align with the indentations 182, 184 on the lower body 170. In the example of FIG. 4, there are two indentations 186, 188 on the upper extension 150; in other examples there can be zero, one, three, four, or more than four indentations on the upper extension 150.

The upper bolt 140 attaches the upper extension 150 to the lower body 170. The upper bolt 140 is generally cylindrical in shape, and can have a hollow interior that extends longitudinally through the upper bolt 140. Such a hollow interior can be useful for accessing the lower bolt 160 while the fixed portion 102 is assembled. The upper bolt 140 is inserted into the upper end of the upper extension 150, and extends distally past the lower end of the upper extension 150 into the lower body 170. The upper bolt 140 has male threads 142 that engage the corresponding female threads 176 in the lower body 170. A practitioner can tighten and loosen the upper bolt 140 by inserting a suitable key into a socket 144 at the upper end of the upper bolt 140. In the example of FIG. 4, the socket 144 is sized and shaped to accommodate an 8 mm hex key; other suitable socket sizes and shapes can also be used.

Figure 5:
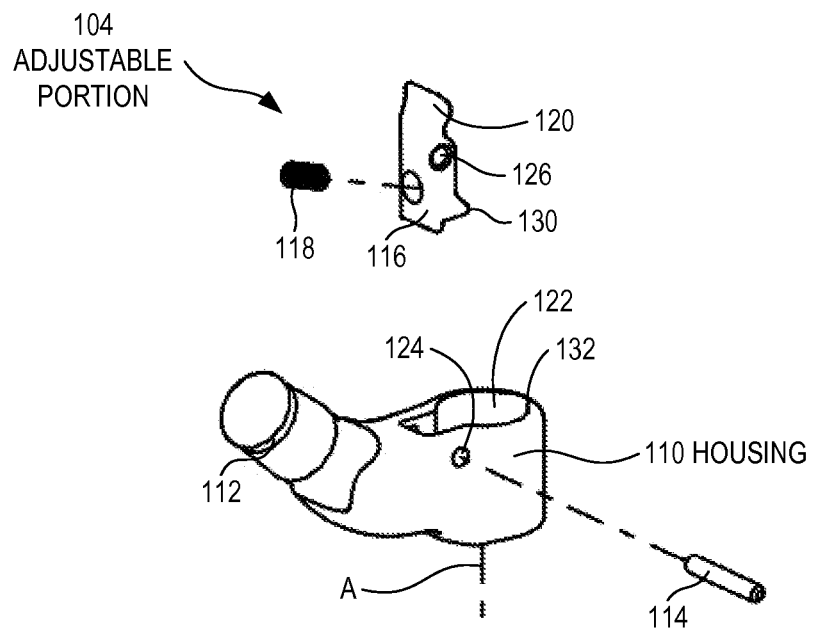
FIG. 5 is an exploded view of the adjustable portion from the adjustable proximal trial of FIG. 3.

FIG. 5 shows adjustable portion 104, which includes a housing 110 and three smaller elements 114, 116, 118.

The adjustable portion 104 includes a movable element 130 that is biased to contact the exterior surface 156, 179 of the fixed portion 102. When the adjustable portion 104 slides to one of the indentations 182, 184, 186, 188, the movable element 130 snaps into the respective indentation to lock the adjustable portion 104 to the fixed portion 102.

The housing 110 has a bore 122 therethrough, which can accommodate the fixed portion 102 during operation. The bore 122 is coaxial with the longitudinal axis (A) of the fixed portion 102. The bore 122 is sized and shaped to accommodate the exterior surface 156, 179 of the fixed portion 102 with a clearance sufficient to allow the adjustable portion 104 to slide vertically along the fixed portion 102. The bore 122 can include a groove or ridge 132 that can mate with the spines 154, 174 on the fixed portion 102.

The housing 110 can extend laterally away from the bore 122 to a mounting ridge 112. A generally spherical head (not shown) can be attached to the mounting ridge 112.

A spring-loaded element 116 is attached to the housing 110. A pivot pin 114 extends through a hole 126 in the spring-loaded element 116, and allows the spring-loaded element 116 to pivot around the pivot pin 114. The pivot pin 114 attaches the spring-loaded element 116 to the housing 110, through hole 124 in the housing 110. The movable element 130 can be disposed at one end of the spring-loaded element 116.

The adjustable portion 104 optionally includes a hand-deployed release mechanism that retracts the movable element 130 from the indentation to unlock the adjustable portion 104 from the fixed portion 102 in order to move it to a different indentation if desired. An example of a release mechanism is a depressable portion, such as a push button, that is pivotally arranged to counteract the biasing effect. For instance, if the biasing element is a spring, and expansion of the spring forces the movable element against the exterior surface of the fixed portion, then the push button can be arranged to compress the spring when pushed, so as to counteract the bias of the spring.

The hand-deployed release mechanism can include one or more of a depressable portion 120, the pivot pin 114, a spring 118, and the movable element 130. Other suitable hand-deployed release mechanisms may also be used. The depressable portion 120 can be disposed at an opposite end of the spring-loaded element 116. The spring 118 biases the spring-loaded element 116 against the housing 110, so that the movable element 130 is biased to contact the exterior surface 156, 179 of the fixed portion 102. During use, a practitioner can use a single hand to release the adjustable portion 104 from the fixed portion 102, for instance, by depressing the depressable portion 120 with a thumb to release the movable element 130 from an indentation in the fixed portion 102.

Figure 6:
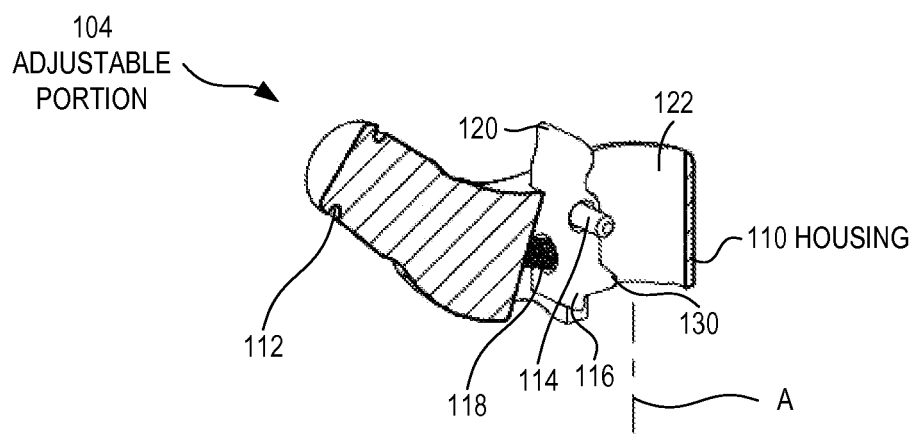
FIG. 6 is a partial cross-section view of the adjustable portion of FIG. 5.

FIG. 6 shows a partial cross-section of the adjustable portion 104 of FIG. 5, in an assembled state.

Figure 7:
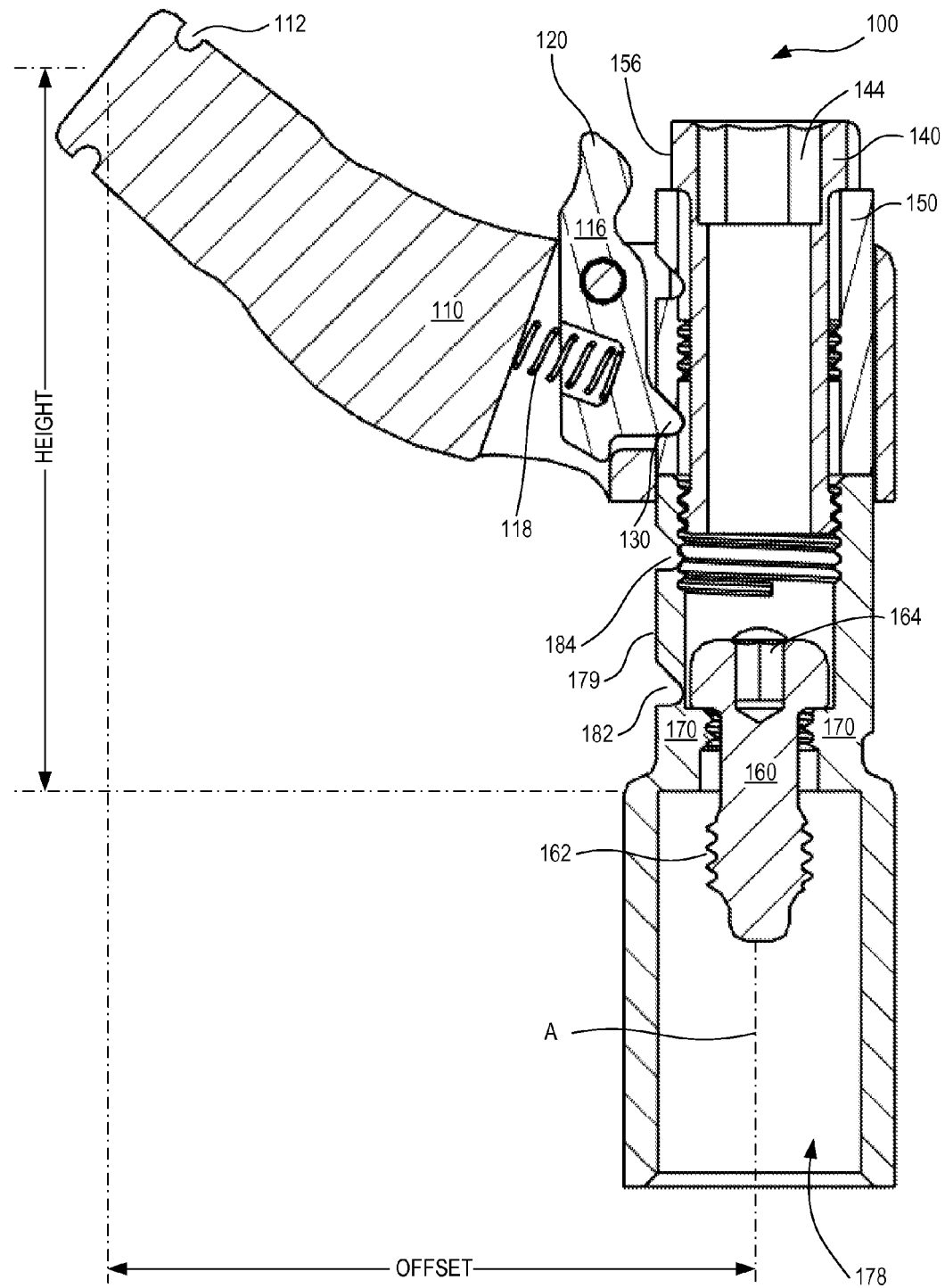
FIG. 7 is a cross-section side view of the assembled adjustable proximal trial of FIGS. 4-6.

FIG. 7 is a side cross-section of an assembled trial implant, to illustrate how the components of FIGS. 4-6 fit together. FIG. 7 also shows an optional feature that can ease adjustments of height during use.

The shapes of the movable element 130 and the indentations 182-188 can influence the locking behavior of the adjustable trial 100. For instance, an upper edge of the movable element 130 and an upper edge of at least one of the indentations 182, 184, 186, 188 can be gently sloped away from the longitudinal axis. For these gentle slopes, when the adjustable portion 104 is locked to the fixed portion 102, applying an upward translational force to the adjustable portion 104 forces the movable element 130 radially outward from the respective indentation 182, 184, 186, 188, and unlocks the adjustable portion 104 from the fixed portion 102. In contrast, a lower edge of the movable element 130 and a lower edge of at least one of the indentations 182, 184, 186, 188 can be more steeply sloped away from the longitudinal axis. For these steep slopes, the movable element 130 remains extended into the respective indentation 182, 184, 186, 188 in the presence of an upward or downward force on the adjustable portion 104. For these cases, the movable element 130 can be refracted by use of the hand-deployed release mechanism. In the example of FIGS. 4-7, the hand-deployed release mechanism includes the depressable portion 120 and the movable element 130. In other examples, the lower edges are gently sloped, while the upper edges are steeply sloped. In still other examples, both the lower and upper edges are gently sloped; for these cases, the adjustable portion 104 can be unlocked from the fixed portion 102 by forcing the adjustable portion 104 upward or downward, which can eliminate the need for a mechanism such as depressable portion 120 in FIGS. 4-6. In still other examples, both the lower and upper edges are steeply sloped.

FIG. 7 also shows an exemplary set of definitions for offset and height. Offset can be defined as a lateral distance between a longitudinal axis (A) of the proximal body and a junction feature found on the adjustable portion 104, such as the mounting ridge 112. Height can be defined as a longitudinal distance between an upper end of the distal stem at the junction feature, such as the mounting ridge 112, found on the adjustable portion 104. In some examples, the height values are equally spaced apart; in other examples, the height values are unequally spaced.

In the configurations of FIGS. 2-7, the adjustable portions have a fixed value of offset. In other configurations, the adjustable portions can have adjustable values of offset (not shown). In some of these configurations, the offset is adjustable in discrete increments that can correspond to offset values available in a set of implantable proximal bodies.

Figure 8:
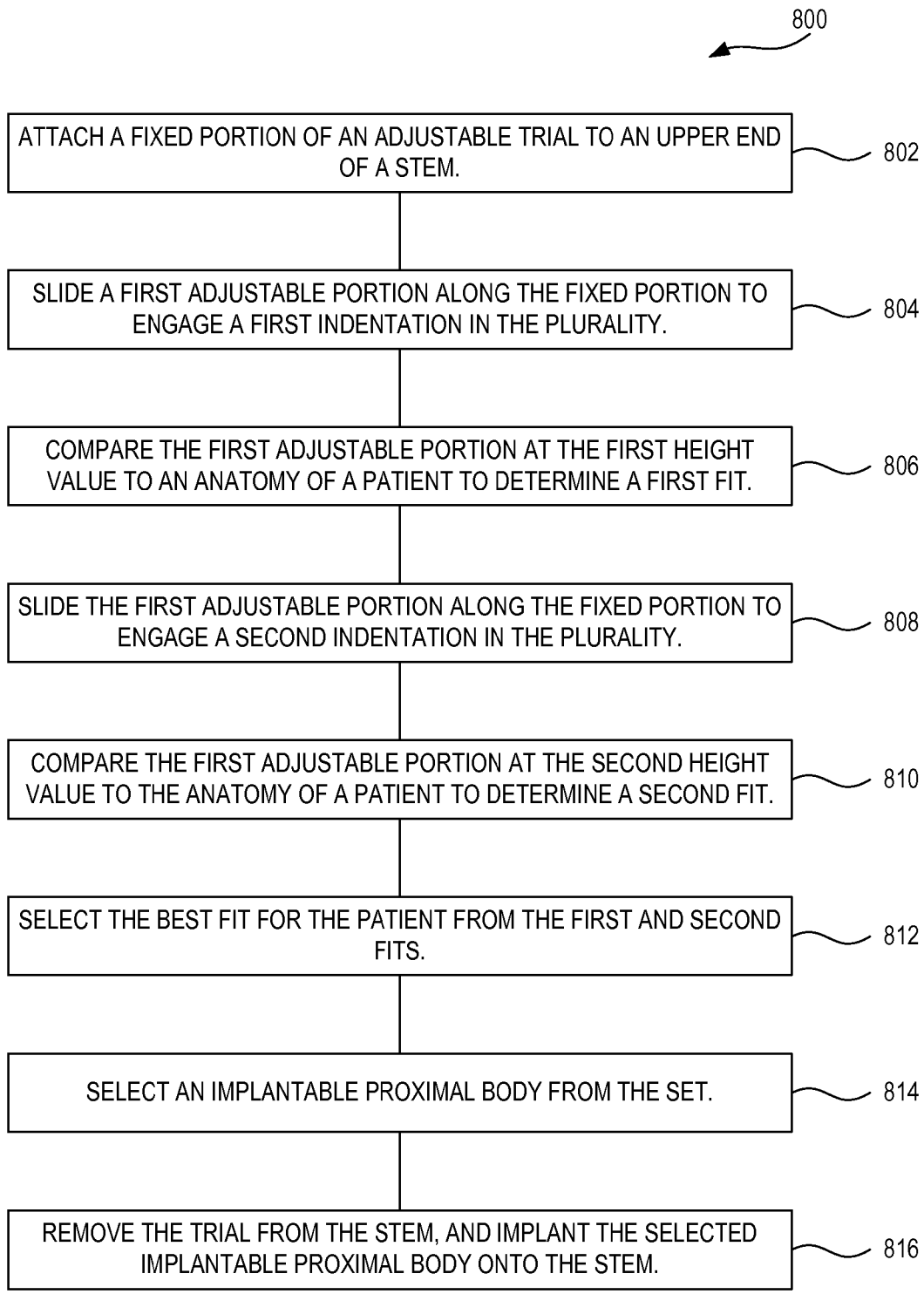
FIG. 8 is a flow chart of a method of using the adjustable proximal trial of FIGS. 4-7.

FIG. 8 is a flow chart of an example method 800 for selecting a suitable height and offset of an implantable proximal body from a set of implantable proximal bodies for hip replacement surgery. Each implantable proximal body in the set has a different combination of offset value, included in a discrete plurality of offset values, and height value, included in a discrete plurality of height values. The selection method 800 can be executed using the generic trial kit 10 and adjustable trial 50, shown in FIGS. 2 and 3, or using the specific exemplary configurations of FIGS. 4-7.

Step 802 attaches a fixed portion of an adjustable trial to an upper end of a stem. The fixed portion can include a plurality of indentations. Each indentation can correspond to a height value in the discrete plurality of height values. Step 804 slides a first adjustable portion along the fixed portion to engage a first indentation in the plurality. The first adjustable portion can have a first height value when the first indentation is engaged. Step 806 compares the first adjustable portion at the first height value to an anatomy of a patient to determine a first fit. Step 808 slides the first adjustable portion along the fixed portion to engage a second indentation in the plurality. The first adjustable portion can have a second height value when the second indentation is engaged. Step 810 compares the first adjustable portion at the second height value to the anatomy of a patient to determine a second fit. Step 812 selects the best fit for the patient from the first and second fits. Step 814 selects an implantable proximal body from the set. The selected implantable proximal body can have the offset value of the first adjustable portion and can have the height value of the first adjustable portion at the best fit. Step 816 removes the fixed portion of the adjustable trial from the upper end of the stem, and implants the selected implantable proximal body onto the upper end of the stem.

The above Detailed Description includes references to the accompanying drawings, which form a part of the Detailed Description. The drawings show, by way of illustration, specific embodiments in which the invention can be practiced. These embodiments are also referred to herein as "examples." Such examples can include elements in addition to those shown or described. However, the inventors also contemplate examples in which only those elements shown or described are provided. Moreover, the inventors also contemplate examples using any combination or permutation of those elements shown or described (or one or more thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, kit, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An adjustable trial for determining a suitable height of an implantable proximal body for hip replacement surgery, comprising:
    a fixed portion configured to removably attach to an upper end of a stem at an upper end of a femur of a patient,
        the fixed portion having a longitudinal axis extending in a vertical direction,
        the fixed portion having an exterior surface,
        the exterior surface including a plurality of indentations thereon at specified locations along the longitudinal axis;
    an adjustable portion configured to slide vertically along the fixed portion; and
    a movable element on the adjustable portion,
        the movable element biased to contact the exterior surface of the fixed portion and configured to snap in a pivotal motion into at least some of the indentations as it slides along the fixed portion,
        the movable element releasably locking the adjustable portion to the fixed portion when the movable element snaps into one of the indentations.

2. The adjustable trial of claim 1, wherein the adjustable portion includes a hand-deployed release mechanism configured to retract the movable element from one of the indentations so as to unlock the adjustable portion from the fixed portion.

3. The adjustable trial of claim 1, wherein for at least one of the plurality of indentations, an upper edge of the movable element and an upper edge of the indentation are shaped so that when the adjustable portion is locked to the fixed portion, applying an upward translational force to the adjustable portion releases the movable element from the indentation so as to unlock the adjustable portion from the fixed portion.

4. The adjustable trial of claim 1, wherein for at least one of the plurality of indentations, a lower edge of the indentation and a lower edge of the movable element are shaped so that when the adjustable portion is locked to the fixed portion, applying a downward translational force to the adjustable portion does not release the movable element from the indentation and does not unlock the adjustable portion from the fixed portion.

5. The adjustable trial of claim 1, wherein the plurality of indentations are arranged along a line parallel to the longitudinal axis.

6. The adjustable trial of claim 1, wherein the adjustable portion and the fixed portion include complementary keying features that prevent rotation about the longitudinal axis between the adjustable portion and the fixed portion.

7. The adjustable trial of claim 1, wherein the adjustable portion includes a bore sized and shaped to accommodate the exterior surface of the fixed portion, the bore and the exterior surface forming a clearance sufficient to allow the adjustable portion to slide vertically along the fixed portion.

8. The adjustable trial of claim 1, wherein the adjustable portion is removable from the fixed portion over an upper end of the fixed portion.

9. The adjustable trial of claim 1, further comprising a plurality of adjustable portions, each adjustable portion in the plurality having a different value of offset.

10. The adjustable trial of claim 1, wherein the fixed portion includes a lower body, and further includes a lower bolt that attaches the lower body to the upper end of the stem, the lower bolt capable of being tightened and loosened from an upper end of the fixed portion, wherein at least one of the plurality of indentations extends over an exterior surface of the lower body.

11. An adjustable trial for determining a suitable height of an implantable proximal body for hip replacement surgery, comprising:
  a fixed portion configured to removably attach to an upper end of a stem at an upper end of a femur of a patient,
    the fixed portion having a longitudinal axis extending in a vertical direction,
    the fixed portion having an exterior surface,
    the exterior surface including a plurality of indentations thereon at specified locations along the longitudinal axis,
    wherein the fixed portion includes a lower body,
    wherein the fixed portion further includes a lower bolt that attaches the lower body to the upper end of the stem,
    the lower bolt capable of being tightened and loosened from an upper end of the fixed portion,
    wherein at least one of the plurality of indentations extends over an exterior surface of the lower body,
    wherein the fixed portion further includes an upper extension, and further includes an upper bolt that attaches the upper extension to the lower body,
    the upper bolt having a hollow interior sized to allow tightening and loosening of the lower bolt therethrough,
    wherein at least one of the plurality of indentations is located on an exterior surface of the upper extension;
  an adjustable portion configured to slide vertically along the fixed portion; and
  a movable element on the adjustable portion,
    the movable element biased to contact the exterior surface of the fixed portion and configured to snap into at least some of the indentations as it slides along the fixed portion,
    the movable element releasably locking the adjustable portion to the fixed portion when the movable element snaps into one of the indentations.

12. A system of adjustable trials for determining a suitable height and offset of an implantable proximal body for hip replacement surgery, comprising:
  a fixed portion configured to removably attach to an upper end of a stem at an upper end of a femur of a patient,
    the fixed portion having a longitudinal axis extending in a vertical direction,
    the fixed portion having an exterior surface,
    the exterior surface including a plurality of indentations thereon at specified locations along the longitudinal axis; and
  a plurality of adjustable portions,
    each adjustable portion in the plurality configured to slide vertically along the fixed portion,
    each adjustable portion in the plurality including a movable element,
    each movable element biased to contact the exterior surface of the fixed portion and configured to snap in a pivotal motion into at least some of the indentations as it slides along the fixed portion,
    each movable element releasably locking the respective adjustable portion to the fixed portion when the movable element snaps into one of the indentations,
    each adjustable portion in the plurality having a different value of offset.

13. The system of adjustable trials of claim 12, wherein each adjustable portion includes a respective hand-deployed release mechanism configured to retract the respective movable element from one of the indentations and unlock the adjustable portion from the fixed portion.

14. The system of adjustable trials of claim 12, wherein for at least one adjustable portion in the plurality and at least one of the plurality of indentations, an upper edge of the movable element and an upper edge of the indentation are shaped so that when the adjustable portion is locked to the fixed portion, applying an upward translational force to the adjustable portion releases the movable element from the indentation and unlocks the adjustable portion from the fixed portion.

15. The system of adjustable trials of claim 12, wherein for at least one adjustable portion in the plurality and at least one of the plurality of indentations, a lower edge of the indentation and a lower edge of the movable element are shaped so that when the adjustable portion is locked to the fixed portion, applying a downward translational force to the adjustable portion does not release the movable element from the indentation and does not unlock the adjustable portion from the fixed portion.

16. The system of adjustable trials of claim 12, wherein the plurality of indentations are arranged along a line parallel to the longitudinal axis.

17. The system of adjustable trials of claim 12, wherein at least one adjustable portion in the plurality and the fixed portion include complementary keying features that prevent rotation about the longitudinal axis between the adjustable portion and the fixed portion.

18. The system of adjustable trials of claim 12, wherein at least one adjustable portion in the plurality includes a bore sized and shaped to accommodate the exterior surface of the fixed portion, the bore and the exterior surface forming a clearance sufficient to allow the adjustable portion to slide vertically along the fixed portion.

* * * * *